US011426335B2

United States Patent
Hodes et al.

(10) Patent No.: US 11,426,335 B2
(45) Date of Patent: Aug. 30, 2022

(54) REDUCED HAIR DAMAGE DURING BLONDING THROUGH USE OF A BIODEGRADABLE COMPLEX FORMER

(71) Applicant: Henkel AG & Co. KGaA, Duesseldorf (DE)

(72) Inventors: Jing Hodes, Hagen (DE); Daniela Kessler-Becker, Leverkusen (DE)

(73) Assignee: HENKEL AG & CO. KGAA, Duesseldorf (DE)

( * ) Notice: Subject to any disclaimer, the term of this patent is extended or adjusted under 35 U.S.C. 154(b) by 0 days.

(21) Appl. No.: 17/279,464

(22) PCT Filed: Sep. 2, 2019

(86) PCT No.: PCT/EP2019/073352
§ 371 (c)(1),
(2) Date: Mar. 24, 2021

(87) PCT Pub. No.: WO2020/064269
PCT Pub. Date: Apr. 2, 2020

(65) Prior Publication Data
US 2022/0031584 A1 Feb. 3, 2022

(30) Foreign Application Priority Data

Sep. 25, 2018 (DE) ...................... 10 2018 123 526.7

(51) Int. Cl.
*A61Q 5/08* (2006.01)
*A61K 8/22* (2006.01)
(Continued)

(52) U.S. Cl.
CPC ............... *A61K 8/22* (2013.01); *A61K 8/365* (2013.01); *A61Q 5/08* (2013.01); *A61Q 5/10* (2013.01)

(58) Field of Classification Search
CPC . A61Q 5/08; A61Q 19/02; A61K 8/22; A61K 8/23; A61K 2800/88; A61K 8/365; A61K 8/36
(Continued)

(56) References Cited

U.S. PATENT DOCUMENTS 7,220,285 B2 * 5/2007 Legrand .................. A61Q 5/08
8/101
7,226,486 B2 * 6/2007 Legrand .................. A61K 8/22
132/202
(Continued)

FOREIGN PATENT DOCUMENTS

EP 1462089 A1 9/2004
EP 2005854 A1 12/2008
(Continued)

OTHER PUBLICATIONS

EPO, International Search Report issued in International Application No. PCT/EP2019/073352, dated Nov. 25, 2019.

*Primary Examiner* — Eisa B Elhilo
(74) *Attorney, Agent, or Firm* — Lorenz & Kopf, LLP

(57) ABSTRACT

The present disclosure relates to cosmetic compositions for the oxidative treatment of keratinous fibers, in particular human hair, comprising at least one salt of a peroxo compound, at least one alkalizing agent and at least one complexing agent. Furthermore, it is an object of the present disclosure to provide a multi-component unit for the oxidative lightening of keratinous fibers, in particular human hair, comprising as first component the cosmetic agent as contemplated herein and as second component an agent comprising $H_2O_2$. In addition, the present disclosure relates to the use of a salt of a polyhydroxylated monocarboxylic acid in a cosmetic composition.

17 Claims, 1 Drawing Sheet

(51) Int. Cl.
*A61K 8/365* (2006.01)
*A61Q 5/10* (2006.01)

(58) Field of Classification Search
USPC .......................................................... 424/62
See application file for complete search history.

(56) References Cited

U.S. PATENT DOCUMENTS

| | | | |
|---|---|---|---|
| 7,803,355 B2* | 9/2010 | Legrand .................. | A61K 8/25 424/62 |
| 2002/0004957 A1* | 1/2002 | Imperial .................. | A61K 8/22 8/405 |
| 2003/0190297 A1 | 10/2003 | Narasimhan et al. | |
| 2004/0253283 A1 | 12/2004 | Muller et al. | |
| 2005/0129644 A1 | 6/2005 | Sabbagh et al. | |
| 2009/0060855 A1* | 3/2009 | Boche ..................... | A61K 8/22 424/62 |
| 2009/0095315 A1* | 4/2009 | De La Mettrie ......... | A61K 8/22 132/208 |
| 2011/0311465 A1* | 12/2011 | Burg ..................... | A61K 8/8152 424/62 |
| 2013/0022565 A1* | 1/2013 | Braida-ValeRio ....... | A61K 8/22 424/62 |
| 2013/0284199 A1* | 10/2013 | Wood ..................... | A61Q 5/10 132/208 |
| 2015/0059794 A1* | 3/2015 | Rose ..................... | A61K 8/33 132/206 |
| 2015/0283049 A1* | 10/2015 | Rose ..................... | A61K 8/365 132/204 |
| 2016/0058688 A1* | 3/2016 | Anderheggen .......... | A61K 8/65 132/208 |
| 2017/0007856 A1* | 1/2017 | Aubert .................. | A45D 37/00 |

FOREIGN PATENT DOCUMENTS

| | | |
|---|---|---|
| EP | 2471502 A1 | 7/2012 |
| WO | 2013167350 A2 | 11/2013 |

* cited by examiner

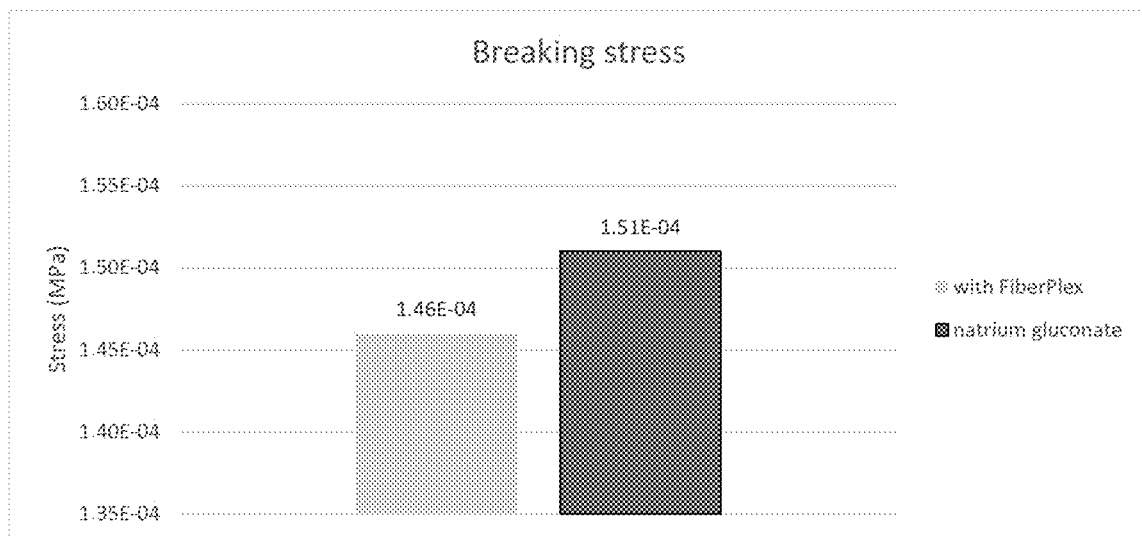

REDUCED HAIR DAMAGE DURING BLONDING THROUGH USE OF A BIODEGRADABLE COMPLEX FORMER

CROSS-REFERENCE TO RELATED APPLICATION

This application is a U.S. National-Stage entry under 35 U.S.C. § 371 based on International Application No. PCT/EP2019/073352, filed Sep. 2, 2019, which was published under PCT Article 21(2) and which claims priority to German Application No. 10 2018 123 526.7, filed Sep. 25, 2018, which are all hereby incorporated in their entirety by reference.

TECHNICAL FIELD

The present disclosure relates to cosmetic compositions for the oxidative treatment of keratinous fibers, in particular human hair, comprising at least one salt of a peroxo compound, at least one alkalizing agent and at least one complexing agent. Furthermore, the present disclosure relates to a multicomponent unit for the oxidative lightening of keratinous fibers, in particular human hair, comprising as first component the cosmetic agent as contemplated herein and as second component an agent comprising $H_2O_2$. In addition, the present disclosure relates to the use of a salt of a polyhydroxylated monocarboxylic acid in a cosmetic composition.

BACKGROUND

Changing hair color represents an important area of modern cosmetics. The appearance of the hair can be adapted to current fashion trends as well as to the individual wishes of the person. In the field of decorative cosmetics, especially bleaching or coloring hair cosmetics, there is a great need for products that are effective and at the same time easy to handle without causing damage. In this field, bleaching and hair coloring systems are available to the consumer, which are extremely effective, but can damage the hair and are under discussion about environmental aspects.

The reactions that cause a bleaching or coloring effect have long been known: The oxidizing agents contained in bleaching agents are able to lighten the hair fiber through the oxidative destruction of the hair's own pigment melanin. For a moderate bleaching effect, the use of hydrogen peroxide—possibly with the addition of ammonia or other alkalizing agents—alone is sufficient as an oxidizing agent; to achieve a stronger bleaching effect, a mixture of hydrogen peroxide and peroxodisulfate salts and/or peroxomonosulfate salts is usually used.

However, aqueous hydrogen peroxide solutions are unstable at the alkaline pH values required for the application, so commercially available oxidative bleaching and dyeing products usually include at least two components. The first component is an acidic oxidant preparation with hydrogen peroxide, which is mixed with an alkaline second component shortly before use.

For permanent dyes, so-called oxidation dyes are used, which are generally available in two parts. The first part used is an alkaline preparation of so-called oxidation dye precursors (OFV), which contains so-called developer components and coupler components that form the actual dyes under the influence of oxidizing agents such as hydrogen peroxide among themselves. The oxidant preparation as the second part, which is often also referred to as the developer, contains at least water and hydrogen peroxide and is acidic for stability reasons. The acid-adjusted oxidizer preparation is mixed with the alkaline-adjusted first part shortly before use. This application mixture is applied to the hair, remains there for a short time and is then rinsed. During this time, the oxidation dye precursors (OFVs) react with each other under the influence of hydrogen peroxide to form oligomers, forming the desired hair color.

The described procedures for oxidative bleaching or lightening or for oxidative coloring attack the hair structure or destroy parts of the hair structure. The users of the cosmetic products are confused to what extent the mechanical resistance is reduced and the surface of the hair becomes rough, preventing shine and increasing the fragility of the hair.

In the processes described, or before any of the processes described are used, the hair or components of the cosmetic products encounter water. The water used contains a quantity of calcium and magnesium ions and a small quantity of copper and iron ions. To a small extent, minute amounts of copper or iron components may also be present in the hair because of previous hair washing. The metallic components can react with peroxides under alkaline conditions during oxidative hair treatment and reactive oxygen species (ROS) can be formed. These ROS react with hair proteins, which can cause hair damage. To suppress these undesirable processes, complexing agents are added to cosmetic products.

A standard complexing agent used in cosmetic products for oxidative hair treatment is ethylenediaminetetraacetate (EDTA). EDTA is under discussion due to its poor biodegradability. In addition, EDTA is not ideal due to its higher affinity for magnesium and calcium compared to copper and iron.

BRIEF SUMMARY

This disclosure provides a cosmetic agent for the oxidative treatment of keratinous fibers comprising:
  at least one salt of a peroxo compound,
  at least one alkalizing agent and
  at least one complexing agent,
  wherein the complexing agent is a salt of a polyhydroxylated monocarboxylic acid having 4, 5 or 6 carbon atoms.

BRIEF DESCRIPTION OF THE DRAWINGS

The present disclosure will hereinafter be described in conjunction with the following drawing FIGURES, wherein like numeral denote like elements, and:

FIG. 1. shows the fracture stress measured using the composition containing sodium gluconate compared to the fracture stress measured using the FiberPlex composition.

DETAILED DESCRIPTION

The following detailed description is merely exemplary in nature and is not intended to limit the disclosure or the application and uses of the subject matter as described herein. Furthermore, there is no intention to be bound by any theory presented in the preceding background or the following detailed description.

Thus, an underlying problem of the present disclosure is to provide a cosmetic composition comprising a powerful complexing agent, wherein the cosmetic composition causes as little stress as possible to the hair, such that an equivalent mechanical strength of the hair is achieved compared to conventional agents, and wherein the performance in terms of the achieved optical appearance of the hair is equivalent or only insignificantly lower compared to the application with conventional agents.

The problem underlying the disclosure is solved by a cosmetic composition according to claim 1. A first object of the disclosure is therefore a cosmetic agent for the oxidative treatment of keratinous fibers, in particular human hair, comprising at least one salt of a peroxo compound, at least one alkalizing agent and at least one complexing agent, wherein the complexing agent is a salt of a polyhydroxylated monocarboxylic acid having 4, 5 or 6 C atoms.

The cosmetic agents as contemplated herein are used for the oxidative treatment of keratinous fibers. In the context of the present disclosure, the term "oxidative treatment" is understood to mean essentially oxidative color changes. These are achieved by bleaching agents and agents for lightening the keratin fibers. The cosmetic composition comprises an oxidizing agent comprising a salt of a peroxo compound, preferably being a persulfate or a percarbonate. If a pure bleaching or lightening is to be carried out, the agents do not contain any further colorants. However, it may also be desired to nuance the keratin fibers in addition to bleaching/lightening. For shading, the cosmetic compositions as contemplated herein may also additionally contain coloring components such as direct dyes and/or oxidation dye precursors. However, the preferred use of the agents is for blonding or lightening.

Keratinous fibers include wool, fur, feathers, and especially human hair. In principle, however, the dyes as contemplated herein can also be used for dyeing other natural fibers, such as cotton, jute, sisal, linen or silk, modified natural fibers, such as regenerated cellulose, nitrocellulose, alkylcellulose, hydroxyalkylcellulose or acetylcellulose.

As a mandatory component, the cosmetic product contains an alkalizing agent that serves to adjust the alkaline pH of the cosmetic product. The cosmetic composition is such that the ready-to-use composition obtained by mixing with water has an alkaline pH value. For this purpose, the cosmetic product contains an alkalizing agent.

When oxidative color modifiers are used, some of the cystine bridges present in the keratin fiber are oxidatively degraded. In this process, the disulfide groups of cystine are oxidatively cleaved and converted into sulfonic acid units. In this way, the cystine linking different peptide strands is oxidized to two discrete, i.e., no longer bridged, cysteic acid units. I.e., when the hair is damaged, the cysteine content in the hair increases. Surprisingly, it has been found that the use of the complexing agent comprising a salt of a polyhydroxylated monocarboxylic acid having 4, 5 or 6 C atoms can reduce the damage to the hair. This beneficial effect can be measured by determining the cysteine content in the hair.

A cosmetic product as contemplated herein shows a lower cysteine content in hair when using a salt of a polyhydroxylated monocarboxylic acid with 4, 5 or 6 C atoms than is found in comparison when using the branded product "Fibreplex Technik". At the same time, the whitening effect (L value, cf. examples) is hardly changed by the application of the new formulation compared to the branded product "Fibreplex". The color difference between hair treated with a cosmetic product as contemplated herein and hair treated with the branded product is less than 2 (cf. examples), i.e., a difference that is usually not detected by an untrained observer.

A polyhydroxylated monocarboxylic acid should be understood to mean carboxylic acids that have a carboxylic acid function and contain at least two OH groups. Preferably, the monocarboxylic acid comprises those having an OH group on each non-carboxyl carbon. Thus, the salt of gluconic acid, the salt of arabonic acid and/or the salt of 2,3,4-trihydroxybutanoic acid are preferably used as complexing agents. The advantage of polyhydroxylated monocarboxylic acids is also that they are easily biodegradable.

When salts whose ions have a specific function are used in the present disclosure, physiologically acceptable counterions are used as their counterions.

Thus, the salts of polyhydroxylated monocarboxylic acids preferentially comprise physiologically acceptable counterions. Thus, alkali or alkaline earth metal cations or ammonium ions are preferred as counterions of the carboxylates. More preferably, the salt of the polyhydroxylated monocarboxylic acid is a gluconate with a physiologically acceptable counterion, most preferably the salt of the polyhydroxylated monocarboxylic acid is sodium gluconate.

The complexing agent used in the cosmetic composition as contemplated herein is a substitute for the ethylenediaminetetraacetate (EDTA) used in conventional compositions. Thus, preferably, no conventional complexing agents are present in the cosmetic composition, and in particular no EDTA is present in the cosmetic composition.

According to a preferred embodiment, the cosmetic composition as contemplated herein contains the complexing agent in an amount of from about 0.1 to about 5-% by weight, preferably from about 0.5 to about 4-% by weight, more preferably from about 1 to about 3-% by weight, based on the total weight of the cosmetic composition. In these volume ranges, the complexing agent is a powerful substitute for conventional complexing agents.

The cosmetic agent contains as oxidizing agent one or more peroxo compounds, preferably a percarbonate and/or a persulfate. According to a preferred embodiment of the present disclosure, the cosmetic composition comprises an inorganic peroxodisulfate salt. The salts of the peroxo compounds thus comprise percarbonates and/or persulfates with an alkali metal or alkaline earth metal cation or an ammonium ion as counterion.

In a preferred embodiment of the present disclosure, the cosmetic composition comprises ammonium peroxodisulfate, potassium peroxodisulfate and/or sodium peroxodisulfate. It has further been found to be advantageous if the cosmetic agent contains at least two persulfates from the group including ammonium persulfate, sodium persulfate and potassium persulfate. Therefore, the cosmetic product more preferably contains a mixture of potassium peroxodisulfate and ammonium peroxodisulfate. It is quite preferred if the cosmetic composition as contemplated herein contains all three persulfates—ammonium persulfate, sodium persulfate and potassium persulfate Ammonium peroxodisulfate is alternatively called ammonium persulfate and has the molecular formula (NH4)2S2O8 Ammonium persulfate has the CAS number 7727-54-0. Potassium peroxodisulfate is alternatively called potassium persulfate and has the molecular formula K2S2O8. Potassium persulfate has the CAS number 7727-21-1. Sodium peroxodisulfate is alternatively called sodium persulfate and has the molecular formula Na2S2O8. Sodium persulfate has the CAS number 7775-27-1.

Persulfates are also preferably used in certain total amounts in the cosmetic composition as contemplated herein, both to optimize lightening performance and to minimize hair damage. According to a preferred embodiment of the present disclosure, potassium peroxodisulfate is used in the cosmetic composition in an amount of from about 20 to about 50% by weight, preferably from about 25 to about 40-% by weight, more preferably from about 29 to about 35-% by weight, based on the total weight of the cosmetic composition. In addition to or as an alternative to the amount of potassium peroxodisulfate, the ammonium peroxodisulfate is used in an amount of from about 1 to about 20-% by weight, preferably from about 3 to about 16-% by weight, more preferably from about 5 to about 15% by weight, based on the total weight of the cosmetic product, in the cosmetic product.

According to a preferred embodiment of the present disclosure, the alkalizing agent is a hydroxide, carbonate, hydrogen carbonate, hydroxy carbonate, silicate or metasilicate of an alkali metal or alkaline earth metal, or the corresponding ammonium salt. Preferably, the alkalizing agent is an alkali or alkaline earth silicate, more preferably sodium silicate, potassium silicate or a mixture of sodium silicate and potassium silicate. More preferably, the alkalizing agent may be a hydrated sodium silicate. This is a water-soluble sodium silicate with an Na2O:SiO2 molar ratio of about 1:2 to about 1:3, more preferably from about 1:2.5 to about 1:2.8. A hydrated sodium silicate particularly suitable as contemplated herein is commercially available under the name Britesil® C 265 (PQ Corporation).

The number of alkalizing agent(s) used is chosen by the specialist depending on the pH value to be set in the cosmetic product ready for use. According to preferred embodiments, the cosmetic composition contains the alkalizing agent in an amount of about 25 to about 50% by weight, preferably from about 30 to about 45% by weight, more preferably from about 35 to about 43% by weight, based on the total weight of the cosmetic composition.

The cosmetic composition is preferably such that the ready-to-use cosmetic composition obtained by mixing with water has an alkaline pH value When the cosmetic composition is intended to be used with a second component comprising $H_2O_2$ or comprising a developer component/coupler component, the ready-to-use cosmetic composition is obtained by mixing the cosmetic composition with the component comprising $H_2O_2$ or by mixing the cosmetic composition with the developer or coupler component. Preferably, the ready-to-use cosmetic agent has a pH value of from about 8 to about 12, particularly preferably a pH value of from about 8.5 to about 11.5, exceptionally preferably a pH value of from about 9 to about 11, in each case measured at about 20° C. For the measurement, the cosmetic agent is slurried in a double amount of water and the pH is measured with a commercially available pH meter at the specified temperature.

According to a preferred embodiment, the cosmetic agent is present in the form of a single component which only needs to be mixed with water to prepare the cosmetic agent ready for use. Mixing with a second, separately packaged preparation can be omitted in this way. When mixed with water, hydrogen peroxide (or "active oxygen") is released from the percarbonates or the persulfates in situ. Because contact with water converts the cosmetic into its ready-to-use form, the cosmetic itself is essentially anhydrous and thus contains less than about 10.0% by weight, more preferably less than about 5-% by weight, even more preferably less than about 2-% by weight of water. For example, about 100 g of an agent as contemplated herein contain at most about 9.9% by weight (=9.9 g) of water. The water content may be conditioned by the raw materials used for the cosmetic composition as contemplated herein. Indeed, various raw materials may contain small amounts of water, for example if they are used in emulsion form, contain water of crystallization, or if water is present as a minor constituent. However, it is of advantage to select the water content in the cosmetic composition as contemplated herein as low as possible.

According to a preferred embodiment of the present disclosure, the bleaching composition further comprises an acrylate-based dispersing copolymer, wherein the dispersing copolymer preferably comprises a copolymer comprising one or more acrylic acid or methacrylic acid units, wherein the dispersing copolymer is more preferably a methacrylic acid/methyl (meth)acrylate copolymer or an acrylic acid/methyl (meth)acrylate copolymer. A particularly preferred commercially available product is Degalan RG S hv. As contemplated herein, the cosmetic agent is to be converted into an agent ready for use by mixing it with water. When mixing powders with water, it may happen that thickening or lumps are formed while other parts of the powder are still present unwetted by water. Wetting with water in general can be difficult. A dispersant is added to improve wetting. The above copolymers and the above commercially available product have proven to be particularly advantageous.

According to a preferred embodiment of the present disclosure, the cosmetic composition further comprises a thickener. Preferably, the ready-to-use cosmetic has a viscosity of from about 5 to about 100 Pa-s, preferably from about 10 to about 50 Pa-s, especially from about 10 to about 20 Pa-s, and more preferably from about 10 to about 16 Pa-s (Brookfield, 22° C., spindle #5, 4 rpm). Both inorganic and organic substances are suitable as thickeners or gelling agents.

On the one hand, thickeners should be present in the cosmetic product largely as free-flowing powder, and on the other hand, they should raise the viscosity of the ready-to-use cosmetic product to a user-friendly range as soon as possible after mixing with water. Preferably, therefore, the thickener is selected from the group including a carboxymethyl cellulose, its Na salt and hydroxymethyl cellulose. Carboxymethyl cellulose (for example Cekol® 50000 from CP Kelco (INCI: Cellulose Gum)) or a combination of carboxymethyl cellulose with a methacrylic acid/methyl methacrylate copolymer (for example Rohagit® S hv ex Evonik (INCI: Acrylates Copolymer) or a combination of the carboxymethyl cellulose with a silica. The thickeners selected above, or the commercially available thickeners mentioned above have proved most advantageous in this respect. The thickener is preferably present in the cosmetic composition in an amount of from about 0.1 to about 10% by weight, more preferably from about 0.4 to about 5% by weight, most preferably from about 1 to about 4-% by weight, based on the total weight of the cosmetic composition.

The cosmetic compositions as contemplated herein may contain further excipients, additives and/or additives. For example, according to preferred embodiments of the present disclosure, the cosmetic compositions may contain fillers. A suitable filler is magnesium carbonate.

Furthermore, the cosmetic agents may contain excipients that suppress the dust formation of the cosmetic agents. In this respect, hydrocarbons are suitable.

The problem underlying the present disclosure is further solved by the subject matter of claim 7. A second object of the present disclosure is therefore a multi-component unit for the oxidative lightening of keratinous fibers, in particular human hair, comprising as a first component a cosmetic agent according to the first object of the present disclosure and as a second component an agent comprising $H_2O_2$.

The multi-component unit includes at least two components. The first component is the cosmetic composition as contemplated herein. The second component is an agent containing $H_2O_2$. The bleaching effect of the multi-component unit as contemplated herein is higher than that of the cosmetic agent as contemplated herein when it is applied as the sole component. Although the cosmetic composition according to a preferred embodiment of the first subject matter of the present disclosure is in the form of a single component, a higher bleaching effect may be desired by the user or user. The separation into two components serves the stability of $H_2O_2$ with a high blonding effect. The multi-component unit also has the advantage of using the polyhydroxylated monocarboxylic acids.

The problem underlying the present disclosure is further solved by the subject matter of claim 8. A third object of the present disclosure is therefore a multicomponent unit for the oxidative coloring of keratinous fibers, in particular human hair, comprising as first component a cosmetic agent according to the first object of the present disclosure and as second component an oxidation dye precursor preferably selected from one or more developer components and optionally one or more coupler components.

The multi-component unit includes at least two components. The first component is the cosmetic composition as contemplated herein. The second component is an agent containing an oxidation dye precursor. This multicomponent unit is advantageously suitable for coloring the keratinous fibers. Although, according to a preferred embodiment of the first subject matter of the present disclosure, the cosmetic composition is in the form of a single component, the user or user may desire color nuance. The separation into two components serves the stability of components of the oxidation dye precursor. The multicomponent unit also has the advantage of using the polyhydroxylated monocarboxylic acids.

The problem underlying the present disclosure is further solved by the subject matter of claim 9. A fourth object of the present disclosure is therefore the use of a salt of a polyhydroxylated monocarboxylic acid having 4, 5 or 6 C atoms, in particular the use of sodium gluconate, as a complexing agent in a cosmetic composition.

The use of polyhydroxylated monocarboxylic acids is particularly suitable as complexing agents in a cosmetic product because of good biodegradability and because a difference in affinity for iron or copper ions is not particularly large compared with affinity for magnesium or calcium ions.

According to a preferred embodiment of the present disclosure, the salts of polyhydroxylated monocarboxylic acids with 4, 5 or 6 C atoms are used in a cosmetic composition as contemplated herein or in a multicomponent unit as contemplated herein. More preferably, the cosmetic composition as contemplated herein is one for oxidative treatment of human hair, more preferably one for oxidative dyeing or one for oxidative lightening of human hair, or more preferably the multicomponent unit as contemplated herein is one for oxidative treatment of human hair, more preferably one for oxidative dyeing or one for oxidative lightening of human hair.

A cosmetic compositions very particularly preferred as contemplated herein comprise at least one of the following embodiments A) to J):

A)
A cosmetic composition for the oxidative treatment of keratinous fibers, in particular human hair, comprising at least one salt of a peroxo compound, at least one alkalizing agent and at least one complexing agent, the complexing agent being a salt of a polyhydroxylated monocarboxylic acid comprising a gluconate having a physiologically acceptable counterion.

B)
A cosmetic composition for the oxidative treatment of keratinous fibers, in particular human hair, comprising at least one salt of a peroxo compound, at least one alkalizing agent and at least one complexing agent, the complexing agent being a salt of a polyhydroxylated monocarboxylic acid comprising a gluconate having a physiologically acceptable counterion, the cosmetic composition being free of ethylenediaminetetraacetate.

C)
A cosmetic composition for the oxidative treatment of keratinous fibers, in particular human hair, comprising at least one salt of a peroxo compound, at least one alkalizing agent and at least one complexing agent, the complexing agent being a salt of a polyhydroxylated monocarboxylic acid comprising a gluconate with a physiologically acceptable counterion, the complexing agent in an amount of from about 0.1 to about 5-% by weight, preferably from about 0.5 to about 4-% by weight, more preferably from about 1 to about 3-% by weight, based on the total weight of the cosmetic agent in the cosmetic composition.

D)
Cosmetic composition for the oxidative treatment of keratinous fibers, in particular human hair, comprising at least one salt of a peroxo compound, at least one alkalizing agent and at least one complexing agent, the salt of the peroxo compound being an inorganic peroxodisulfate salt, preferably ammonium peroxodisulfate, potassium peroxodisulfate and/or sodium peroxodisulfate, more preferably a mixture of potassium peroxodisulfate and ammonium peroxodisulfate, and wherein the complexing agent is a salt of a polyhydroxylated monocarboxylic acid comprising a gluconate with a physiologically acceptable counterion.

E)
A cosmetic composition for the oxidative treatment of keratinous fibers, in particular human hair, comprising at least one salt of a peroxo compound, at least one alkalizing agent and at least one complexing agent, the salt of the peroxo compound being a mixture of potassium peroxodisulphate and ammonium peroxodisulphate, potassium-peroxo-disulphate being present in an amount of from about 20 to about 50% by weight, preferably from about 25 to about 40-% by weight, more preferably from about 29 to about 35-% by weight, and the ammonium peroxodisulphate being present in an amount of from about 1 to about 20% by weight, preferably from about 3 to about 16-% by weight, more preferably from about 5 to about 15-% by weight, in each case based on the total weight of the cosmetic composition. %, preferably from about 3 to about 16 wt. %, more preferably from about 5 to about 15 wt. %, each based on the total weight of the cosmetic, is contained in the cosmetic, and wherein the complexing agent is a salt of a polyhydroxylated monocarboxylic acid comprising a gluconate having a physiologically acceptable counterion, wherein the complexing agent is present in an amount of from about 0.1 to about 5-% by weight, preferably from about 0.5 to about 4-% by weight, more preferably from about 1 to about 3-% by weight, based on the total weight of the cosmetic composition, in the cosmetic composition.

F)
A cosmetic composition for the oxidative treatment of keratinous fibers, in particular human hair, comprising at least one salt of a peroxo compound, at least one alkalizing agent and at least one complexing agent, the salt of the peroxo compound being an inorganic peroxodisulfate salt, preferably ammonium peroxodisulfate, potassium peroxodisulfate and/or sodium peroxodisulfate, more preferably a mixture of potassium peroxodisulfate and ammonium peroxodisulfate, wherein the alkalizing agent is a water-soluble sodium silicate having a molar ratio $Na_2O:SiO_2$ of from about 1:2 to about 1:3, more preferably from about 1:2.5 to about 1:2.8, even more preferably a sodium or potassium disilicate, wherein the complexing agent is a salt of a polyhydroxylated monocarboxylic acid comprising a gluconate having a physiologically acceptable counterion.

G)

Cosmetic composition for the oxidative treatment of keratinous fibers, in particular human hair, comprising at least one salt of a peroxo compound, at least one alkalizing agent and at least one complexing agent, the salt of the peroxo compound being a mixture of potassium peroxodisulphate and ammonium peroxodisulphate, potassium peroxodisulphate being present in an amount of from about 20 to about 50% by weight, preferably from about 25 to about 40-% by weight, more preferably from about 29 to about 35-% by weight, and the ammonium peroxodisulphate being present in an amount of from about 1 to about 20% by weight, preferably from about 3 to about 16-% by weight, more preferably from about 5 to about 15-% by weight, in each case based on the total weight of the cosmetic composition. %, preferably from about 3 to about 16 wt. %, more preferably from about 5 to about 15 wt. %, in each case based on the total weight of the cosmetic composition, wherein the alkalizing agent is a water-soluble sodium silicate with a molar ratio $Na_2O:SiO_2$ of from about 1:2 to about 1:3, more preferably from about 1:2.5 to about 1:2.8, even more preferably a sodium or potassium disilicate, which is present in the cosmetic composition in an amount of from about 25 to about 50 wt. %, preferably from about 30 to about 45 wt. %. %, preferably from about 30 to about 45 wt. %, more preferably from about 35 to about 43 wt. % by weight, based on the total weight of the cosmetic composition, in the cosmetic composition, and wherein the complexing agent is a salt of a polyhydroxylated monocarboxylic acid comprising a gluconate with a physiologically acceptable counterion, the complexing agent being present in an amount of from about 0.1 to about 5-% by weight, preferably from about 0.5 to about 4-% by weight, more preferably from about 1 to about 3-% by weight, based on the total weight of the cosmetic composition, in the cosmetic composition.

H)

Cosmetic composition for the oxidative treatment of keratinous fibers, in particular human hair, comprising at least one salt of a peroxo compound, at least one alkalizing agent and at least one complexing agent, the salt of the peroxo compound being a mixture of potassium peroxodisulphate and ammonium peroxodisulphate, potassium peroxodisulphate being present in an amount of from about 20 to about 50% by weight, preferably from about 25 to about 40-% by weight, more preferably from about 29 to about 35-% by weight, and the ammonium peroxodisulphate being present in an amount of from about 1 to about 20% by weight, preferably from about 3 to about 16-% by weight, more preferably from about 5 to about 15-% by weight, in each case based on the total weight of the cosmetic composition. %, preferably from about 3 to about 16 wt. %, more preferably from about 5 to about 15 wt.-% by weight, each based on the total weight of the cosmetic product, the alkalizing agent being present in the cosmetic product in an amount such that the pH value of the cosmetic product is between from about 8 and about 12, preferably between from about 8.5 and about 11.5 and more preferably between from about 9 and about 11, when the cosmetic is brought into its ready-to-use form, and wherein the complexing agent is a salt of a polyhydroxylated monocarboxylic acid comprising a gluconate with a physiologically acceptable counterion, the complexing agent being present in an amount of from about 0.1 to about 5-% by weight, preferably from about 0.5 to about 4-% by weight, more preferably from about 1 to about 3-% by weight, based on the total weight of the cosmetic composition, in the cosmetic composition.

I)

A cosmetic composition for the oxidative treatment of keratinous fibers, in particular human hair, comprising at least one salt of a peroxo compound, at least one alkalizing agent, at least one thickener and at least one complexing agent, wherein the salt of the peroxo compound is an inorganic peroxodisulfate salt, preferably ammonium peroxodisulfate, potassium peroxodisulfate and/or sodium peroxodisulfate, more preferably a mixture of potassium peroxodisulfate and ammonium peroxodisulfate, wherein the thickener is selected from the group including a carboxymethylcellulose, its Na salt and hydroxy methylcellulose, and wherein the complexing agent is a salt of a polyhydroxylated monocarboxylic acid comprising a gluconate with a physiologically acceptable counterion.

J)

A cosmetic composition for the oxidative treatment of keratinous fibers, in particular human hair, comprising at least one salt of a peroxo compound, at least one alkalizing agent, at least one thickener, at least one dispersing copolymer based on acrylates and at least one complexing agent, the salt of the peroxo compound being an inorganic peroxodisulfate salt, preferably ammonium peroxodisulfate, potassium peroxodisulfate and/or sodium peroxodisulfate, more preferably a mixture of potassium peroxodisulfate and ammonium peroxodisulfate, wherein the thickener is selected from the group including a carboxymethylcellulose, its Na salt and hydroxy methylcellulose, wherein the dispersing copolymer is more preferably a methacrylic acid/methyl (meth)acrylate copolymer or an acrylic acid/methyl (meth)acrylate copolymer, and wherein the complexing agent is a salt of a polyhydroxylated monocarboxylic acid comprising a gluconate having a physiologically acceptable counterion.

Where amounts are listed in embodiments A) to J), the amounts add up to 100-% by weight. Where appropriate, the cosmetic compositions of these embodiments contain adjuvants, additives and/or additives. For example, the cosmetic agents may contain fillers, so that the total amount adds up to 100-% by weight.

Features relating to preferred embodiments of the first subject matter of the present disclosure, which are described above only with respect thereto, apply, of course, mutatis mutandis to the second, third and fourth subject matter as features of preferred embodiments. In particular, the objects of the present disclosure relate to cosmetic compositions that are free of EDTA.

The following examples are intended to explain the objects of the present disclosure without limiting them in any way.

EXAMPLES

1. Formulation
The following formulations were prepared (unless otherwise stated, the quantities correspond to % by weight)
Blonding Powder

|  | Example 1 |
| --- | --- |
| Ammonium persulfate + 0.5% Silica | 10.0 |
| Potassium persulphate | 32.0 |
| Sodium silicate [1] | 36.0 |
| Sodium hexametasulfate | 0.2 |
| Methyl methacrylate, methacrylic acid Copolymer [2] | 1.0 |
| Carboxymethyl cellulose (Na salt) [3] | 2.0 |
| Sodium gluconate | 1.6 |
| Silica, hydrophilic | 0.4 |
| Paraffinum Liquidum | 3.6 |
| Magnesium carbonate | ad 100 |

[1] Britesil C 265 (molar Ratio SiO$_2$/Na$_2$O = 2.65), PQ Corporation
[2] Degalan RG S hv, Evonic
[3] Cekol 50000, CP Kelco

2. Application

The blonding powder according to Example 1 above and a Fibreplex series blonding powder were mixed with hydrogen peroxide in a ratio of 1:2 (1 part by weight of blonding powder with 2 parts by weight of hydrogen peroxide). The ready-to-use bleaching agents obtained in this way were each applied to hair strands (Kerling euro-natur 7-0 from Fischbach & Miller, light brown) and left to act for 45 minutes. After that, the strands of hair washed with a standard shampoo and water.

Each hair strand was colorimetrically measured before and after bleaching (spectrophotometer type Spectraflash 450 from X-right, type exact). The color difference (ΔE value) was determined from the Lab values obtained during the measurements.

3. Blonding Performance

|  | Cysteic acid amount [%] | ΔE-Value | L |
| --- | --- | --- | --- |
| Fibreplex comparison | 6.8 |  | 69.25 |
| Example 1 | 5.6 | 0.58 | 69.26 |

The L value indicates the brightness of the color (L=0, black; L=100, white). The higher the L value of the treated strand, the more the strand was blonde.

The ΔE value used to assess the color intensity is derived from the L*a*b* colorimetric values as follows:

$$\Delta E = [(L_i - L_0)^2 (a_i - a_0)^2 + (b_i - b_0)]^{1/2}$$

$L_0$, $a_0$ and $b_0$: Color readings before bleaching.
$L_i$, $a_i$ and $b_i$: Colorimetric values after bleaching.

The ΔE value indicates the color difference that exists between the untreated and the treated hair strand. The greater the ΔE value, the greater the color difference (i.e., the color gap) between the uncolored and the colored skin and the stronger the bleaching power. The color difference between hair treated with a cosmetic product as contemplated herein (Example 1) and hair treated with the branded product is less than 2, i.e., a difference that is usually not detected by an untrained observer.

The cysteic acid content of keratin fibers or hair strands can be determined by near-infrared spectroscopy (NIR spectroscopy). NIR spectroscopy allows direct quantification of cysteic acid content without altering or destroying the structure of the hair by analysis (see also Y. Miyamae et al. IFSCC Magazine, 9, 219 (2006) and Y. Miyamae et al, Appl. Opt. Spectroscopy, 61, (2) 212 (2007)). Here, the hair is irradiated with infrared radiation (heat radiation in the near-infrared range). In this way, not only the surface of the hair is analyzed, but the NIR radiation also penetrates the hair due to the small absorption cross-section. The radiation excites the components of the hair to vibrate, absorbing radiation of defined wavelengths. Cysteic acid leads to characteristic absorptions in the NIR spectrum. Based on the strength of these absorptions, the content of cysteic acid in the keratin fiber can be determined.

After applying the products, the hair fibers were soaked in water for at least 1 hour. They were then stretched at a constant rate of 10 mm/to the break point (i.e., the stress at the fiber break point was measured). The greater the breaking stress, the stronger the hair fibers. The results of the measurement are shown in FIG. 1. FIG. 1 shows the fracture stress measured using the composition containing sodium gluconate compared to the fracture stress measured using the FiberFlex composition.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

The invention claimed is:

1. A cosmetic agent for the oxidative treatment of keratinous fibers comprising:
   a salt of a peroxo compound,
   an alkalizing agent and
   a gluconate with a physiologically acceptable counterion and wherein the cosmetic agent does not comprise ethylenediaminetetraacetate, and
   wherein the gluconate is present in the cosmetic agent in an amount of from about 0.1 to about 5% by weight based on the total weight of the cosmetic agent.

2. The cosmetic agent according to claim 1, wherein the gluconate is sodium gluconate.

3. The cosmetic agent according to claim 1, wherein the gluconate is present in the cosmetic agent in an amount of from about 1 to about 3% by weight based on the total weight of the cosmetic agent.

4. The cosmetic agent according to claim 1, wherein the salt of the peroxo compound is an inorganic peroxodisulfate salt which is optionally ammonium peroxodisulfate, potassium peroxodisulfate and/or sodium peroxodisulfate, and wherein if potassium peroxodisulfate is utilized it is present in an amount of from about 20 to about 50% by weight and wherein if ammonium peroxodisulfate is utilized it is present in an amount of from about 1 to about 20% by weight, in each case based on the total weight of the cosmetic agent.

5. The cosmetic agent according to claim 1, wherein the alkalizing agent is a hydroxide, carbonate, hydrogen carbonate, hydroxy carbonate, silicate or metasilicate of an alkali or alkaline earth metal or the corresponding ammonium salt.

6. The cosmetic agent according to claim 1, wherein the alkalizing agent is present in the cosmetic agent in an amount of from about 25 to about 50% by weight based on the total weight of the cosmetic agent, and wherein the pH of the cosmetic agent is between about 8 and about 12 when the cosmetic agent is dissolved and/or slurried in a double amount of water.

7. A multicomponent unit for the oxidative lightening of keratinous fibers comprising as a first component the cosmetic agent according to claim 1 and as a second component an agent comprising $H_2O_2$.

8. A multicomponent unit for the oxidative coloring of keratinous fibers comprising as a first component the cosmetic agent according to claim 1 and as a second component an oxidation dye precursor selected from one or more developer components and one or more coupler components.

9. The cosmetic agent according to claim 1, wherein the gluconate is present in the cosmetic agent in an amount of from about 0.5 to about 4% by weight based on the total weight of the cosmetic agent.

10. The cosmetic agent according to claim 1, wherein the salt of the peroxo compound is ammonium peroxodisulfate, potassium peroxodisulfate and/or sodium peroxodisulfate, wherein if potassium peroxodisulfate is utilized it is present in an amount of from about 25 to about 40% by weight and wherein if ammonium peroxodisulfate is utilized it is present in an amount of from about 3 to about 16% by weight, each based on the total weight of the cosmetic agent.

11. The cosmetic agent according to claim 1, wherein the salt of the peroxo compound is a mixture of potassium peroxodisulfate and ammonium peroxodisulfate, wherein the potassium peroxodisulfate is present in an amount of from about 29 to about 35% by weight and the ammonium peroxodisulfate is present in an amount of from about 5 to about 15% by weight, each based on the total weight of the cosmetic agent.

12. The cosmetic agent according to claim 1, wherein the alkalizing agent is a water-soluble sodium silicate having a molar ratio $Na_2O:SiO_2$ of from about 1:2 to about 1:3.

13. The cosmetic agent according to claim 1, wherein the alkalizing agent is a water-soluble sodium silicate having a molar ratio $Na_2O:SiO_2$ of from about 1:2.5 to about 1:2.8.

14. The cosmetic agent according to claim 1 wherein the alkalizing agent is a sodium or potassium disilicate.

15. The cosmetic agent according to claim 1, wherein the alkalizing agent is present in an amount of from about 30 to about 45% by weight based on the total weight of the cosmetic agent and the pH of the cosmetic agent is from about 8.5 to about 11.5 when the cosmetic agent is dissolved and/or slurried in a double amount of water.

16. The cosmetic agent according to claim 1, wherein the alkalizing agent is present in an amount of from about 35 to about 43% by weight based on the total weight of the cosmetic agent and the pH of the cosmetic agent is from about 9 to about 11 when the cosmetic agent is dissolved and/or slurried in a double amount of water.

17. The cosmetic agent according to claim 1, wherein
the gluconate is sodium gluconate;
the sodium gluconate is present in an amount of from about 1 to about 3% by weight based on the total weight of the cosmetic agent;
the salt of the peroxo compound is a mixture of potassium peroxodisulfate and ammonium peroxodisulfate, wherein the potassium peroxodisulfate is present in an amount of from about 29 to about 35% by weight and the ammonium peroxodisulfate is present in an amount of from about 5 to about 15% by weight, each based on the total weight of the cosmetic agent;
the alkalizing agent is a water-soluble sodium silicate having a molar ratio $Na_2O:SiO_2$ of from about 1:2.5 to about 1:2.8;
the alkalizing agent is present in an amount of from about 35 to about 43% by weight based on the total weight of the cosmetic agent; and
the pH of the cosmetic agent is from about 9 to about 11 when the cosmetic agent is dissolved and/or slurried in a double amount of water.

* * * * *